Figure 1:
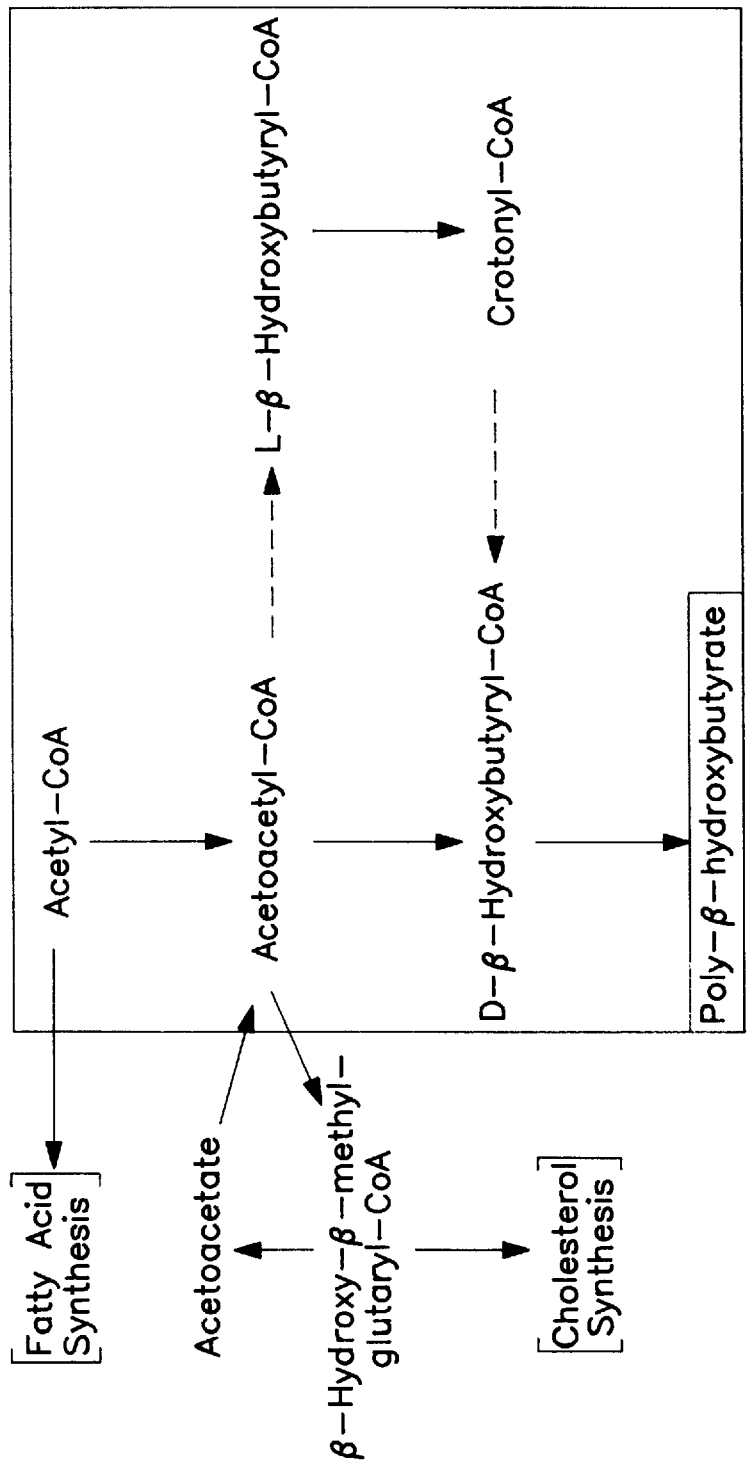

United States Patent [19]

Reusch

[11] Patent Number: 5,880,269
[45] Date of Patent: Mar. 9, 1999

[54] ANTIBODIES FOR PHB

[75] Inventor: Rosetta N. Reusch, Okemos, Mich.

[73] Assignee: Board of Trustees operating Michigan State University, East Lansing, Mich.

[21] Appl. No.: 888,362

[22] Filed: May 26, 1992

Related U.S. Application Data

[60] Division of Ser. No. 809,269, Dec. 16, 1991, which is a continuation-in-part of Ser. No. 615,411, Nov. 19, 1990, abandoned.

[51] Int. Cl.$^6$ .................................................. C07K 16/18
[52] U.S. Cl. ................................. 530/389.8; 530/389.5; 530/389.1; 530/412
[58] Field of Search ........................... 530/388.2, 388.4, 530/389.1, 389.5, 389.8, 866, 412, 417, 387.1

[56] References Cited

PUBLICATIONS

Harlew et al., Antibodies, A Laboratory Manual, Cold Spring Harbor, USA pp. 55–123, and 626–631 (1988).
Harlow et al., Antibodies, a Laboratory Manual, Cold Spring Harbor, USA pp. 55–123, and 626–631 (1988).
Steinberg, P., In "Hypercholesterolemia and Atherosclerosis. Pathogenesis and Prevention", Churchill Livingstone, New York, pp. 5–25 (1987).
Epstein, F. H., In "International conference on Atherosclerosis", Carlson, L. A., et al., eds, Raven Press, New York (1978) (pp. 351–356).
Wallace, R. B. and Anderson, R. A., Epidemiol Rev 9:95 (1987).
Kannel, W. B., Am Cardiol 52:9B (1983).
Mahley, R. W., et al., J. Lip. Res. 21:970 (1980).
Dahlen, G. H., et al., Circulation 74:758–65 (1986).
Reardon, M. F., Circulation 71:881–8 (1985).
Dawes, E. A., et al., Adv. Microb. Physiol. 10:135 (1973).
Schubert, P., et al., J. Bacteriol. 170:5837 (1988).
Moskowitz, G. J., et al., Biochemistry 8:2748 (1969).
Packter, N. M., In "Biosynthesis of Acetate–derived Compounds", John Wiley, New York pp. 143–150 (1973).
Reusch, R. N., et al., J. Bacteriol 156:778 (1983).
Reusch, R. N., et al., J. Bacteriol. 168:553 (1986).
Reusch, R. N., et al., Can. J. Microbiol. 33:435 (1987).
Reusch, R. N., et al., Proc. Natl. Acad. Sci. USA 85:4176 (1988).
Reusch, R. N., Soc. Exp. Biol. Med. 191:377 (1989).
Tanio, T., et al., Eur. J. Biochem. 124:71–77 (1982).
Engvall and Perlman, Immunoschemistry 8:871 (1971).
Bluhm, T. L., et al., Macromolecules 19:2871 (1986).
Karr, D. G., et al., Appl. Environ. Microbiol. 46:1339 (1983).
Bush, T. L., et al., E. Clin. Chem. 34:8B (1988).
Blackburn, H., In "Hypercholesterolemia and Atherosclerosis" (ed. Steinberg, D., et al), Churchill Livingstone, New York (1987).
Kelly, J. L. and Kruski, A. W., Meth. in Enz. 128, 170–181 (1986).
Law, J. H. and Slepecky, R. A., J. Bacteriol. 82, 33–36 (1961).
Friedewald, W. T., et al., Clin. Chem. 18, 499–502 (1972).
Current Protocols in Molecular Biology (Ausubel, F. M., Brent, R., Kingstom, R. E. Moore, D. D., Seidman, J. G., Smith, J. A. and Struhl, K. eds). pp. 10.2–10.8 John Wiley & Sons, NY (1989).
Mill, G. L. and Lane, P. A., A Guidebook to lipo–protein technique. pp. 1–76. Elsevier, NY (1984).
Peters, T., Adv. Prot. Chem. 37, 161–245 (1984).
Schwick, H. G. and Haupt, H., in The Plasma Proteins, vol. IV pp. 168–220. Academic Press, NY (1984).
Hay, R., et al., in Biochemistry and Biology of Plasma Lipoproteins (Scanu A. M. and Spector, A. A. eds) pp. 11–51, Marcel Dekker, NY (1986).
Scanu A. M. and Spector, A. A. eds) pp. 1–10, Marcel Dekker, NY (1986).
Eisenberg, S., Meth. in Enz. 129, 347–366 (1986).
Nickerson, K. W., App. Envir. Microbiol. 43, 1208–1209 (1982).
Steiner, G., et al., Meth. in Enz. 129,395–420 (1986).
Fless, G. M., and Scanu, A. M., in Biochemistry and biology of Plasma Lipoproteins (Scanu, A. M. and Spector A. A. eds) pp. 73–83, Marcel Dekker, NY (1986).
Carter, D. C. and He, X. M., Science 249, 302–303 (1990).

*Primary Examiner*—Sally P. Teng
*Attorney, Agent, or Firm*—Ian C. McLeod

[57] ABSTRACT

An analytical method for detecting the presence poly-beta-hydroxybutyrate (PHB) which can be used as an indicator of atherosclerotic risk. A novel antibody to PHB for use in the preferred analytical method is described.

9 Claims, 5 Drawing Sheets

ANTIBODIES FOR PHB

CROSS-REFERENCE TO RELATED APPLICATION

This is a divisional of copending application Ser. No. 07/809,269 filed on Dec. 16, 1991, which is a continuation-in-part of U.S. application Ser. No. 07/615,411, filed Nov. 19, 1990.

BACKGROUND OF THE INVENTION

(1) Field of the Invention

The present invention relates to a method for evaluating atherosclerotic risk by means of the detection of levels of PHB in blood serum in humans. In particular the present invention relates to a method which utilizes an antibody for such detection.

(2) Prior Art

Atherosclerotic cardiovascular disease (CVD) is a leading cause of death in industrialized countries. Though it is current opinion that a variety of initiating agents and multiple interactive mechanisms contribute to the formation of atheromatous plaques, the critical role of lipids in the process is not disputed (Steinberg, P., In "Hypercholesterolemia and Atherosclerosis. Pathogenesis and Prevention", Churchill Livingstone, New York, pp 5–25 (1987)). Apparently, the focal deposition of lipids transported into the vessel wall by lipoproteins plays an important role in the initiation of an atherosclerotic lesion.

The precise mechanisms by which lipids induce the lesions, and the identity of the lipidic atherogenic agent(s) is not yet clear. Epidemiologic and clinical studies have established that the incidence of atherosclerosis is positively related to serum cholesterol levels (Epstein, F. H., In "International conference on Atherosclerosis", Carlson, L. A., et al., eds, Raven Press, New York (1978)), with the risk of disease correlating more strongly with an increase in the low-density lipoprotein fraction (LDLC) and/or a decrease in the high-density fraction (HDLC) (Wallace, R. B. and Anderson, R. A., Epidemiol Rev 9:95 (1987)). Results from the Framingham Study suggest that the ratio of LDLC/HDLC is the best predictor in men closely followed by TC/HDLC (Kannel, W. B., Am Cardiol 52:9B (1983)). However, a number of other lipidic risk factors have also been identified such as beta-very low density lipoprotein (beta-VLDL) (Mahley, R. W., et al., J. Lip. Res. 21:970 (1980)), triglycerides (TG) in intermediate-density lipoprotein (IDL) in women (Dahlen, G. H., et al., Circulation 74:758–65 (1986)), Lp (a) (Reardon, M. F., Circulation 71:881–8 (1985)) and apolipoproteins A-1 and B (Wallace R. B. and Anderson, R. A., Epidemiol. Rev. 9:95 (1987)).

PHB is an amphiphillic lipid which is well-known as a high molecular weight storage polymer in bacteria, in which it accumulates in cytoplasmic granules (MW range of 60,000 to 1,000,000) (Dawes, E. A., et al., Adv. Microb. Physiol. 10:135 (1973)). PHB is synthesized from acetyl-CoA by two major pathways—a three step synthesis as e.g. in *Alcaligenes eutrophos* or *Zoologea ramigera* (Schubert, P., et al., J. Bacteriol. 170:5837 (1988)) or a five step synthesis as in *Rhodospirillum rubrum* (Moskowitz, G. J., et al., Biochemistry 8:2748 (1969)).

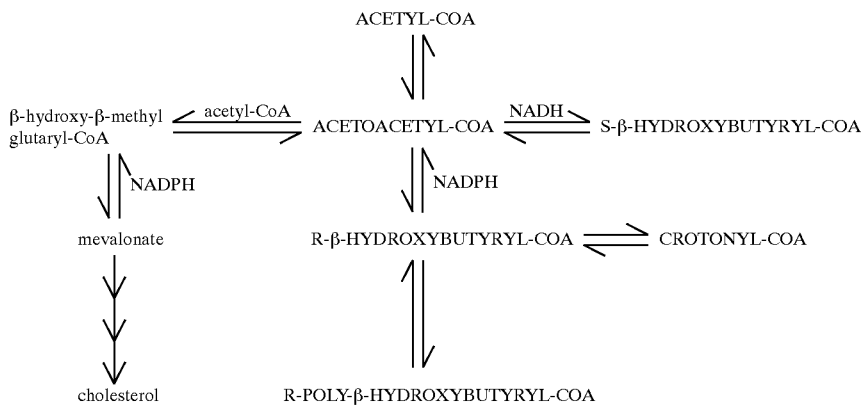

The schematic diagram above shows the relationship between PHB and cholesterol syntheses. The first step in both biochemical pathways is the condensation of acetyl-CoA to acetoacetyl-CoA catalyzed by beta-ketothiolase. In the case of PHB synthesis, this step is followed by reduction with NADPH or NADH, whereas cholesterol synthesis requires that a third acetyl-CoA condense with acetoacetyl-CoA before the reductive step (Packter, N. M., In "Biosynthesis of Acetate-derived Compounds". John Wiley, New York pp 145–150 (1973)). Sharing the common intermediate-acetoacetyl-CoA-causes both PHB and cholesterol synthesis to be regulated by changes in intracellular concentrations of acetyl-CoA.

The work leading up to the discovery of PHB in the serum lipoproteins is summarized here. It has been established that a low molecular weight species of PHB (MW ca 15,000) exists in the plasma membranes of bacteria. This is complexed with calcium polyphosphate of approximately the same molecular size (Reusch, R. N., et al., J. Bacteriol 156:778 (1983); Reusch, R. N., et al., J. Bacteriol. 168:553 (1986); Reusch, R. N., et al., Can. J. Microbiol. 33:435 (1987); Reusch, R. N., et al., Proc. Natl. Acad. Sci. U.S.A. 85:4176 (1988)). The location, composition and putative structure of this complex suggest it may be involved in $Ca^{2+}$ and $PO_4^{2-}$ transport, and consequently may play a role in calcium regulation and signaling. The potential importance of the PHB membrane complex coupled with the ubiquitous distribution of the PHB monomer, R-beta-hydroxybutyrate, prompted us to search for PHB and the PHB complex in eukaryotes. We surveyed a variety of plant and animal tissues and found that PHB and its complex were widely distributed in biological cells (Reusch, R. N., Soc. Exp. Biol. Med. 191:377 (1989)). The intracellular location of PHB and its complexes in beef liver cells was primarily in the membrane fractions, particularly in mitochondria and microsomes with lesser but significant amounts in plasma membranes.

IN THE DRAWINGS

FIG. 1 is a diagram showing the derivation of PHB.

Figure 2:
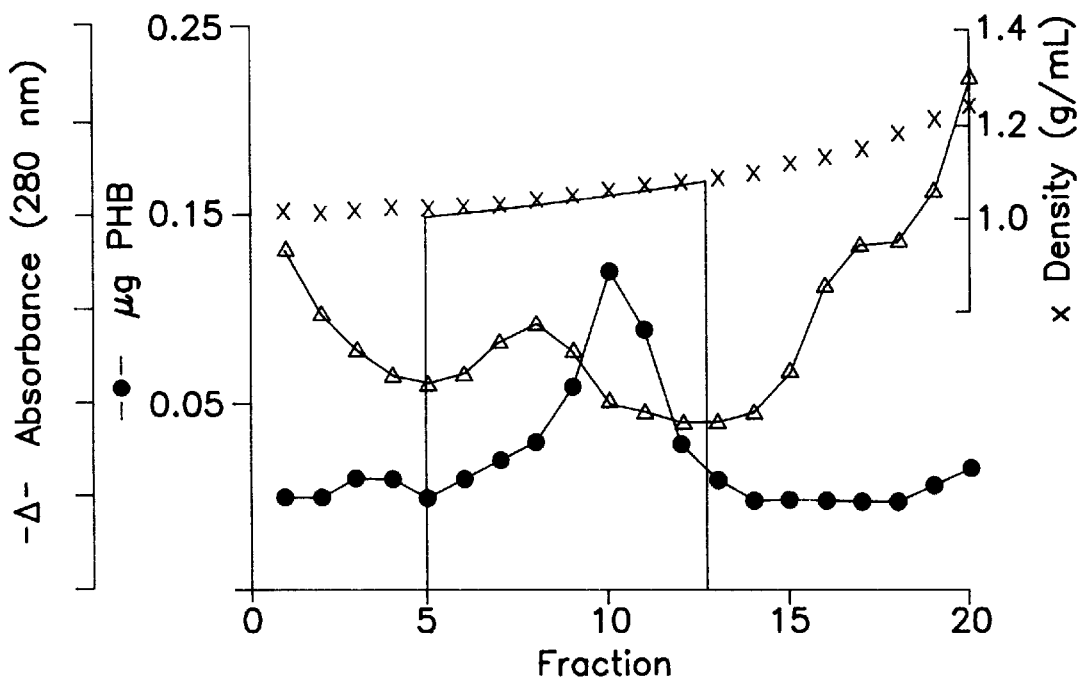

FIG. 2 shows a distribution of PHB and protein in density gradient fractions of human plasma. Plasma (pool from 10 individuals) was separated in sodium bromide density gradients (1.005 1.24 g/mL) by ultracentrifugation at 38,000 rpm at 14° C. to equilibrium. PHB was isolated from individual fractions by chloroform extraction, and determined by chemical assay (see Methods). Shaded area designates LDL fractions.

Figure 3:
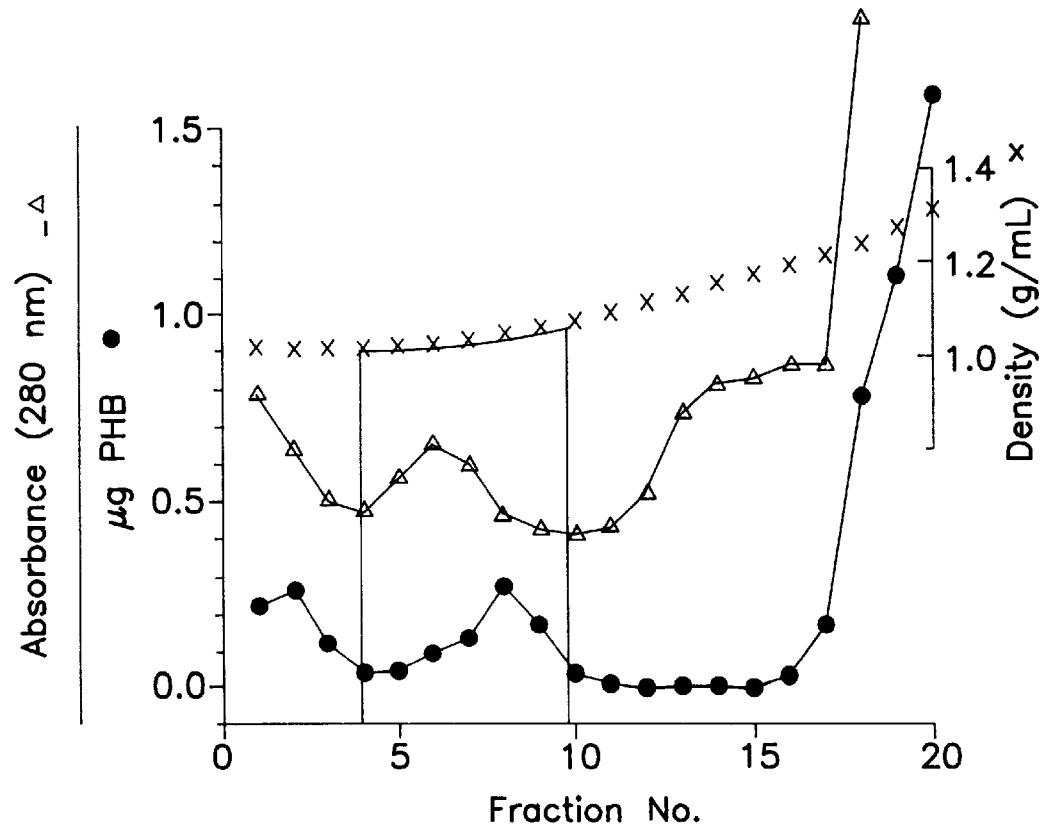

FIG. 3 shows the same distribution as in FIG. 2. Plasma was pooled from 12 individuals. Densities ranged from 1.005 to 1.34 g/mL PHB was determined by dot-blot Elisa immunoassay (see Methods). Shaded area designated LDL fractions.

Figure 4:
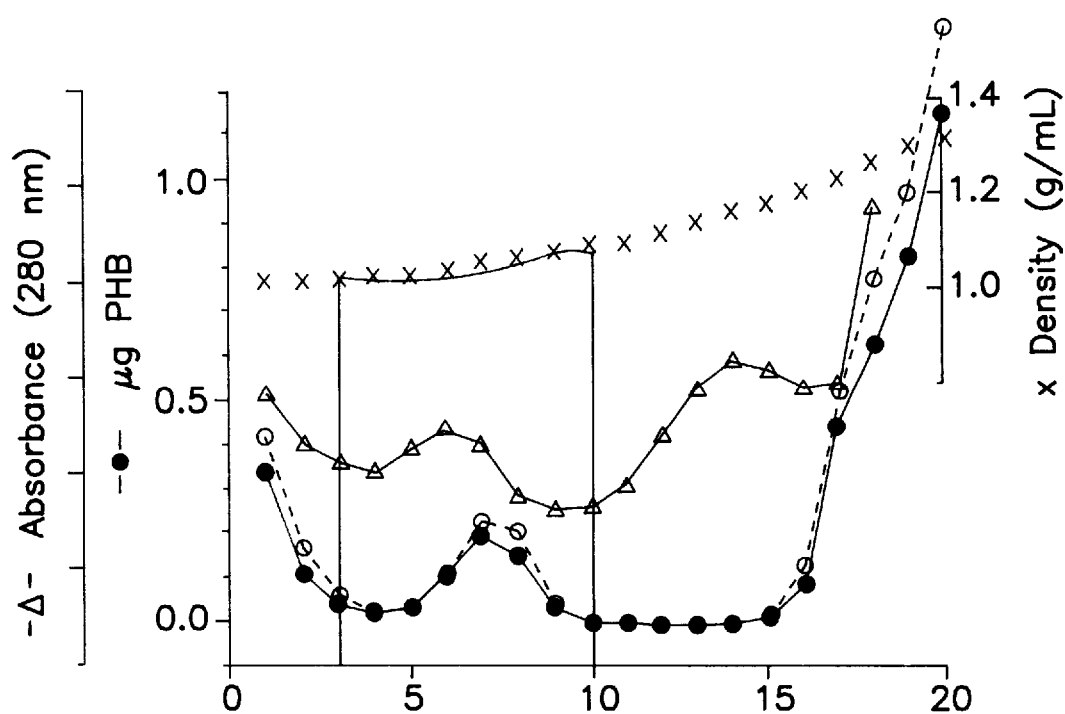

FIG. 4 shows the same distribution as in FIG. 2. Plasma was pooled from 14 individuals. Densities ranged from 1.005 to 1.34 g/mL. Solid line—PHB determined by direct hydrolysis of dialyzed, lyophilized fractions (see Methods). Dotted line—PHB determined by dot-blot ELISA immunoassay. Shaded area designates LDL fractions.

Figure 5:
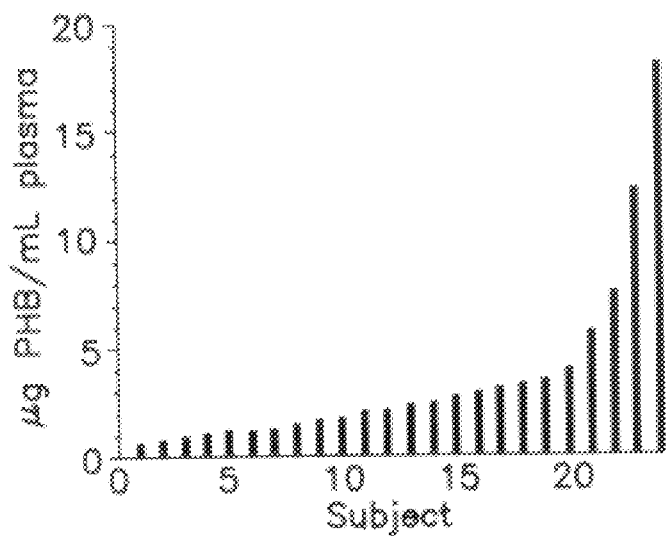

FIG. 5 shows the total PHB in plasma of 24 normal adults, determined by dot-blot Elisa immunoassay.

Figure 6:
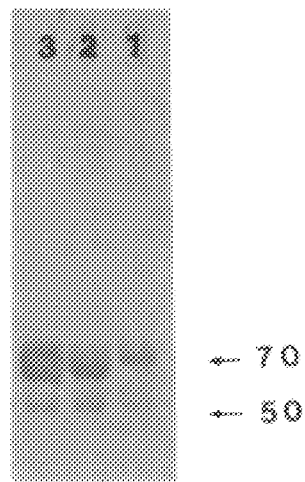

FIG. 6 shows PHB-binding proteins in high density fractions of human plasma. Fractions 18, 19 and 20 (Lanes 1, 2, 3) of densities 1.22, 1.26 and 1.31 g/mL, respectively, separated by SDS-PAGE on 10% acrylamide (30% acrylamide, 0.8% bisacrylamide), electrophoretically transferred to nitrocellulose membranes, and probed with anti-PHB F(ab')$_2$.

Figure 7:
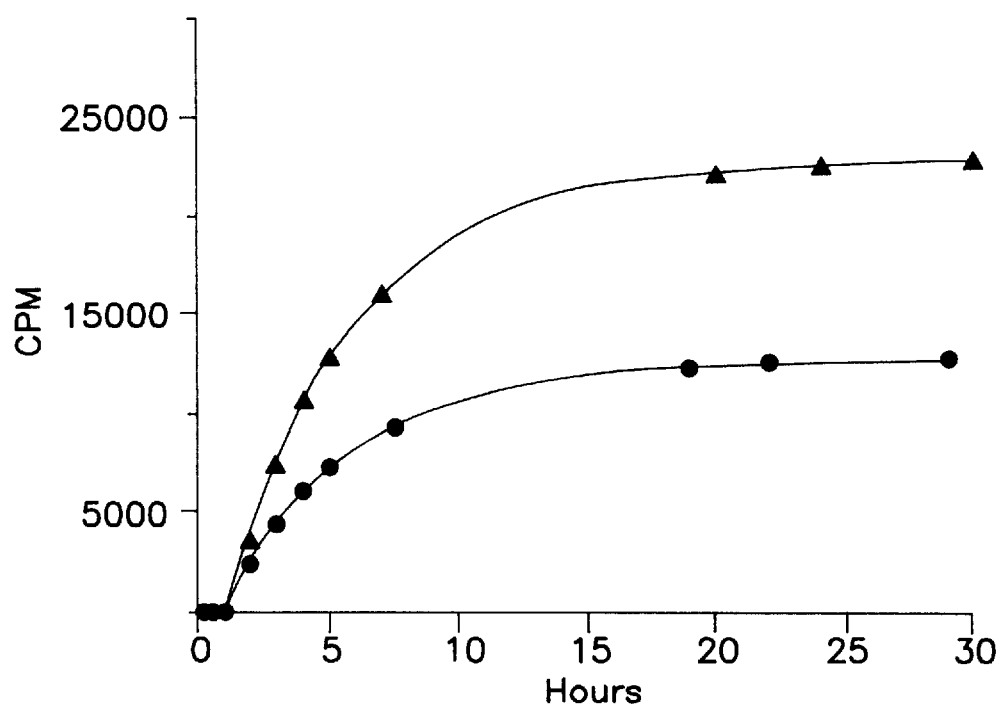

FIG. 7 shows the transfer of $^{14}$C-PHB (4150 cpm/μg PHB) from chloroform to a solution of albumin in 10 mM Hepes, pH 7.2. ●10 mg/mL HSA; ▲40 mg/mL BSA.

OBJECTS

The present invention relates to an analytical method for detecting a potential for atherosclerotic disease (CVD) in humans by means of the amount of PHB in the blood serum. The present invention also relates to a novel antibody against PHB which is used in the preferred method. These and other objects will become increasingly apparent from the following description.

General Description

The present invention relates to an analytical method for diagnosing a potential for atherosclerotic cardiovascular disease, referred to as CVD, in a human patient which comprises: determining an amount of poly-beta-hydroxybutyrate, referred to as PHB, in the blood serum or a fraction thereof of the patient; and comparing the amount of PHB in the blood serum of the patient to that of individuals in a low risk group for CVD to determine whether the patient has an elevated level of the PHB and thus the potential for CVD.

Further the present invention relates to a method for preparing an antibody against poly-beta-hydroxybutyrate, referred to as PHB, which comprises: providing deproteinated PHB; disrupting the PHB in water to form an aqueous suspension of segments of the PHB; centrifuging the suspension to remove solids and provide a supernatant containing suspended segments of PHB; coupling the suspended segments to an invertebrate protein antigen to provide a conjugate; injecting a mammal with the conjugate in suspension; and isolating an antibody against poly-beta-hydroxybutyrate from the blood of the mammal.

Finally the present invention relates to an improvement in a procedure for analyzing human blood serum which comprises determining an amount of poly-beta-hydroxybutyrate in the blood serum or blood plasma.

The wide distribution of PHB in mammalian membranes raised the question of whether pHB is transported by the serum lipoproteins. VLDL, LDL and HDL fractions of human serum were examined and PHB was found predominantly in the LDL. The properties of PHB-extreme insolubility in water, 'solubility' in membranes and lipids, ability to act as a hydrogen bond acceptor and to form coordinate bonds-suggested that the polymer may act as a nidus for the accumulation of lipids in the intima. Samples of plaque from human carotid arteries were analyzed and were found to contain PHB in amounts considerably greater than in tissues.

PHB has escaped notice in mammalian systems despite extensive examination of these lipids by many investigators for several reasons: 1) PHB has been widely regarded as only a bacterial lipid so that prevailing lipid protocols do not test for it; 2) PHB has no distinctive atoms or functional groups which would draw attention to it, since the only functional moiety is the ester group which is a very common linkage in lipids; 3) PHB is present in very small amounts which are below the detection limits of most analytical methods; 4) PHB tends to associate with other lipids, coextracting and cochromatographing with them, which disperses the small amount of PHB among a large pool of lipids making it even less noticeable.

In the method for producing the antibody which is preferably used in the analytical method of the present invention, the PHB is conjugated with an invertebrate antigen, such as Keyhole *Limpet haemocyanin*, to provide antigenicity and to prevent the formation of antibodies which would recognize a mammalian antigen conjugate. The PHB is disrupted, preferably by sonication, to provide segments of the PHB which are coupled with the invertebrate antigen. The conjugate is precipitated and separated and then injected into a mammal, for example a rabbit. The polyclonal antibodies are isolated from the serum of the mammal and then the antibody against PHB is isolated from serum. This is accomplished in a conventional manner such that non-specific antibodies are removed by binding to various antigens.

The antibody thus produced is preferably treated with a proteinase to remove non-specific fractions of the antibody and then the specific fractions are separated from the non-specific fractions. The preferred enzymes are pepsin and papain and the preferred fractions are F(ab')$_2$ and F(ab) produced by the enzymes, respectively. The resulting antibody fractions are very specific for the PHB and exhibit little or no cross-reactivity with other antigens.

The method of producing the antibody is unique in that the invertebrate antigen is linked to segments of PHB and used for injection into the mammal. These conjugates are a suspension and not a solution and yet were able to produce the selective antibodies. It was unexpected that the PHB segments, produced by disrupting PHB, would produce the selective antibodies.

There are various types of solid phase assays where the PHB is absorbed directly onto a solid phase or indirectly by means of an antibody linked to the solid phase. Microliter plates or strips, tubes, particles, dip sticks, beads, microliter slides and fibers made of nylon nitrocellulose, glass or quartz have been used. Liquid phase assays including competitive binding assays for a single site antigen with linked antibody and non-competitive binding using an antigen with two or more sites and excess antibodies have been used. All of this is well known to those skilled in the art.

The PHB antisera can be polyclonal or monoclonal raised in various animals. The antibodies can be IgG or IgM and can include $F(ab')_2$ or $F(ab)$ fragments of the antibodies. The antibodies can be prepared by hybridomas or of antibody producing genes which are isolated from procaryotes or eucaryotes, preferably the latter. They can be labeled or unlabeled.

The antibody or anti-antibody can be labeled with enzymes, substrates or co-factors such as alkaline phosphatase, peroxidase, beta-galactosidase, glucose oxidase, urease, Penicillin G, as well as metals and dye sols such as colloidal gold or palanil luminous Red G. Radionucleotides such as iodine-125 and tritium can be used. Pre-luminescent labels such as isoluminol derivatives and acridinium esters can be used as labels. Electrochemically active compounds can be used as labels, such as dimethyl aminomethylferrocene.

Various amplification systems can be used such as multiple site avidin biotin amplification and enzyme where a primary coupled enzyme produces a regeneratable substrate for a secondary enzyme. Various detection systems can be used such as optical, electrical, thermal and acoustic detectors with the appropriate signal generating label for the antibody. All of these are well known to those skilled in the art.

The antibodies produced are preferably used in the analytical method for quantitating the PHB. It is clear that other methods for analysis of the PHB could be used, such as chromatographic methods known to the prior art. Such methods are tedious and insensitive and the antibody methods are much preferred.

An alternate to the immunoassay is an enzyme assay for poly-beta-hydroxybutyrate (PHB) uses PHB depolymerases and beta-hydroxybutyrate oligomer hydrolase to completely degrade the polymer to beta-hydroxybutyrate (BHB), and then BHB is determined by established methods. Depending on the system, it may be necessary to first determine or remove endogenous BHB from the sample. Since BHB is very soluble in water, alcohol, acid, etc. and PHB is very insoluble in all of these, the endogenous BHB can be removed by centrifugation or filtration, or PHB can first be precipitated with perchloric or trichloracetic acid and then removed by centrifuging or filtering, etc.

In this assay, poly-beta-hydroxybutyrate (PHB) is degraded to dimers and trimers by PHB depolymerases. There are two types of depolymerase enzymes, PHB depolymerase I and II. PHB depolymerase I is an endogenous enzyme which degrades only 'structured' PHB such as is found in PHB granules in the cytoplasms of bacteria. PHB depolymerase II is an exogenous enzyme which will degrade 'unstructured' PHB (Tanio, T., et al., *Eur. J. Biochem.* 124:71–77 (1982)). PHB depolymerase I have been isolated from the gram-negative bacteria, *Azotobacter vinelandii*, and PHB depolymerase II and BHB oligomer hydrolase has been isolated from the supernatant of gram-negative *Alcaligenes faecalis*. There are a number of established methods for determining BHB, the most well-known being oxidation with BHB dehydrogenase (commercially available from Sigma, St. Louis, Mo.) with NAD as hydrogen acceptor. The amount of product NADH is then measured by well established methods.

Specific Description

The following are Examples of the preferred antibody and assay method of the present invention.

EXAMPLE 1

Preparation of poly-beta-hydroxybutyrate (PHB) antibody

The following is the preferred method for the preparation of the antibody to PHB. PHB is a linear head-to-tail polymer of R-(-)-beta-hydroxybutyrate of natural occurrence. There are presently three kinds of PHBs of interest: granular deposits of high molecular weight (60,000 to 1,000,000) found in the cytoplasms of a wide variety of bacteria; polymer in the molecular weight range of 15,000 to 18,000 found in serum and in the membranes of prokaryotic and eukaryotic cells; and low molecular weight oligomers resulting from degradation of the above. Antibodies were raised to PHBs in each of these classes by isolating and purifying the form of interest and binding it covalently to a carrier protein.

The starting materials were PHB granules, obtained from *Azotobacter vinelandii* or PHB from Alcaligenes (Sigma, St. Louis, Mo.). The PHB-containing material was suspended in 0.01M Tris, 0.005M EDTA, 0.5% SDS, pH 7.8 and treated with proteinase K (200 µg/ml) to degrade adhering proteins which might be antigenic. Higher-molecular weight PHBs were prepared from the purified granules. These were suspended in distilled water and agitated vigorously with a Vortex mixer. Heavier particulates were allowed to settle and the cloudy supernatant was decanted and further "homogenized" by repeated passage through an 18 gauge and then a 21 gauge hypodermic needle. PHBs in the lower molecular weight ranges were prepared by fractionation of chloroform solutions of purified polymer. The solution was first subjected to gentle ultrasonication, and then chromatographed on a high pressure non-aqueous size exclusion column (Altex, ANSPEC, Ann Arbor, Mich.), Spherogel GPC, 7.7 mm×30 cm; using chloroform as the elution solvent and polyethylene-glycols of known molecular weight (Sigma) as standards. A fraction containing polymer in the desired molecular weight range, e.g. 12,000 to 20,000 for anti-serum PHBs, was collected. The PHBs were precipitated by addition of methanol (5×), collected by centrifugation, and suspended in distilled water as described above. Short-chain oligomers were prepared by strong ultrasonication of suspensions of purified PHB in distilled water. Particulate matter was pelleted by low-speed centrifugation, and the clarified supernatant containing the oligomers was decanted.

An aliquot of the aqueous suspension, assayed at 100–150 µg PHB, was added to 1 mg Keyhole Limpet Hemocyanin (KLH) (Megathura crenulata; Sigma), and to this was added 6 mg N-hydroxysulfosuccinimide (sulpho-NHS; Pierce, Rockford, Ill.) and 100 mg 1-ethyl-3-(3-dimethyl-aminopropyl carbodiimide (EDC; Pierce). The mixture was incubated at room temperature overnight. The precipitate was collected by centrifugation, and suspended in 2 ml distilled water (Milli Q) by the procedure described above.

A New Zealand white rabbit was bled from the ear vein to obtain preimmune serum. The rabbit was then inoculated at multiple sites with an emulsion of KLH-PHB conjugate and Freund's complete adjuvant (1 ml each). The inoculation was repeated after two weeks with an emulsion of KLH-PHB conjugate and Freund's incomplete adjuvant (1 ml each). After ten days, blood was obtained from the ear vein, allowed to coagulate at room temperature for 2 hours and then incubated overnight at 4° C. The serum was decanted and clarified by low-speed centrifugation. The IgG fraction was precipitated by the addition of ammonium sulfate (33% saturation), collected by centrifugation, dissolved in phosphate buffered saline (PBS), and dialyzed overnight against the same buffer. The IgG was further purified by affinity chromatography on immobilized Protein A (Pierce IgG purification kit), and then absorbed against KLH bound to agarose. Next, the IgG was digested with immobilized pepsin (10 mg IgG to 0.125 ml gel, total volume 1.5 ml) in 20 mM sodium acetate buffer, pH 4.2 overnight at 37° C., and the F(ab')$_2$ fragments were separated from undigested IgG and Fc fragments by chromatography on immobilized protein A (Pierce F(ab')$_2$ Preparation kit). Finally, the F(ab')$_2$ fraction was dialyzed overnight against PBS, pH 7.0. The F(ab')$_2$ fraction of the preimmune serum was prepared identically.

The PHB-antisera were of low titer (1:500) but showed high specificity and avidity. There was considerable cross-reactivity between the antisera prepared against PHBs of high and low molecular weight ranges so that each of them could be used to detect PHB's of any molecular size, albeit at some loss in sensitivity. The most notable differences were found between antisera to oligomers and to polymers of moderate length (<20,000), which suggests that the dominant epitopes are present in low molecular weight forms.

EXAMPLE 2

Immunoassay For PHB in Serum Using Goat Anti-Rabbit IgG

The Bio-Dot microfiltration apparatus (BioRad, Rockville Center, N.Y.) can be used for any application requiring immobilization of proteins, nucleic acids, or polymers to membrane solid phases. Nitrocellulose membranes are most commonly used for soluble antigens and nucleic acids, as they can be assayed by RIA, EIA or FIA.

The Bio-Dot Slot Format blotting apparatus has an evenly spaced sample template, designed for easy blot sample comparison.

MATERIALS

1. TBS NaCl 29.24 g,
   Tris Base 2.42 g
   Total volume 1000 ml in water.
2. Blocking solution: 3% gelatin in TBS. Add 3.0 g gelatin to 100 mL TBS, heat at 37° C. to dissolve the gelatin.
3. Washing buffer (TTBS): 0.05% Tween-20 in TBS.
4. Antibody buffer: 1% gelatin in TTBS.
7. Second antibody (Goat anti-rabbit IgG (H+L)-alkaline phosphatase) from Boehringer Mannheim, (Cincinnati, Ohio).
8. Alkaline phosphatase conjugate substrate Kit from Bio-Rad: No. 170-6432.
   AP. color reagent A 1 mL
   AP. color reagent B 1 mL
   AP. color buffer 100 mL
9. Supported Nitrocellulose-1 membrane size: 0.45 u. From GIBCO BRL (Gaithersburg, Md.) Cat. No. 1465 MF.

PROCEDURE

1. Prewet filter papers and nitrocellulose membrane in TBS.
2. Assemble under vacuum.
3. Rehydrate with 200 uL 1× TBS.
4. Apply Ag (PHB) in 1× TBS in serial dilutions, 50 ul/well, starting at 1:10 dilution of stock PHB solution.
5. Gravity drain off (2 hrs or overnight).
6. Under vacuum, take out membrane.
7. Oven dry for 30 min at 90° C.
8. Block all parts in Block solution for 1 hour at 37° C. with gentle agitation.
9. Wash with TTBS once for 5 minutes.
10. Cut off No Ab, no Enzyme conjugant anti-Ab, Normal Rabbit IgG sections.
11. Apply first Ab (anti PHB-IgG, purified) (ca 5 ul/mL).
12. Cover tank with foil, and incubate at 37° C. for 35 minutes 15.
13. Wash with TTBS 4 times, each 5 minutes.
14. Apply second Ab (Alkaline phosphatase-conjugated anti-first Ab rabbit IgG). 1:1000 dilution in Ab buffer.
15. Cover tank with foil and incubate at 37° C. for 35 minutes.
16. Wash with TTBS 4 times, each 5 minutes.
17. Final wash with TBS 2× to remove Tween.
18. Add Alkaline Phosphatase substrate.

This procedure provided satisfactory quantitative identification of PHB.

EXAMPLE 3

Immunoassay for PHB in Serum Using Sheep Anti-rabbit IgG

1. The samples (plasma, serum or other) were serially diluted with TBS buffer (20 mM Tris HCl, pH 7.5, 500 mM NaCl), and 10 to 100 μl portions of each dilution were applied to prewetted supported nitrocellulose membrane (BRL, Gaithersburg, Md.) (9×12 cm; 0.45 μm) in a Bio-Dot apparatus (Bio-Rad, Rockville Centre, N.Y.)l. Buffer and PHB standards (0–100 pg) were applied to one lane. The samples were allowed to filter through the membrane by gravity flow. The membrane was then removed from the apparatus under vacuum and heated at 90° C. for 30 minutes. The membrane was preferably wet with 5.25% sodium hypochlorite (Clorox™) and incubated at 37° C. for 30 minutes to avoid testing with preimmune serum. The membrane was washed 1× with TBS and 2× with TTBS, blocked by incubation with 3% gelatin (Bio-Rad IEF grade) in TTBS buffer (0.5% Tween 20 in TBS) for one hour at 37° C., and then washed 1× with TTBS. Portions of the membrane to be used as controls (first antibody only, second antibody only, or preimmune serum IgG (F(ab')$_2$ followed by second antibody) were cut off and treated separately as indicated. The remainder of the membrane was incubated with rabbit anti-PHB IgG, (F(ab')$_2$) fragment 2 μl/mL in 1% gelatin/TTBS, for 30 minutes at 37° C., and then washed 4 times with TTBS buffer. The membrane was incubated with the second antibody which was sheep anti-rabbit IgG conjugated to alkaline phosphatase, F(ab')$_2$ fragment (Sigma), 1 μl/mL in 1% gelatin/TTBS, for 30 minutes at 37° C. This antiserum had been preabsorbed with human serum proteins, human serum albumin and human IgG. After 4 washes with TTBS, and two with TBS to remove excess detergent, color was developed with the enzyme substrate BCIP (5-bromo-4-chloro-3-indolyl phosphate) and NBT (nitro blue tetrazolium) Bio Rad alkaline phosphatase conjugate substrate kit). The reaction was stopped by adding distilled water. Assuming that the single antibody controls were negative, the amount of PHB was determined by comparison of the color generated with that of the standards, after correction for non-specific background absorption as estimated from the reaction with the preimmune serum.

2. The samples (plasma, serum or other) were serially diluted with TBS buffer, and 2 μl portions of each dilution were applied to dry nitrocellulose membrane. Buffer and PHB standard (0–100 pg) were applied to one lane. The membrane was then treated in the same manner as above and the results were the same.

EXAMPLE 4

Sandwich Elisa for Detecting PHB

Enzyme-linked immunosorbent assays (ELISA), which were first described by Engvall and Perlman (1971) (Immunochemistry 8:871 (1971)), are rapidly replacing most other forms of immunoassays for a variety of reasons. These include: (a) stability of reagents, (b) versatility of enzyme immunoassay formats that allows for detective quantification of variety of antigens and antibodies, (c) speed and ease of use, (d) safety and (e) minimum equipment or facility requirements. There are two kinds of ELISA, direct and sandwich, ELISA. The direct ELISA involves the binding of antigen directly to the microtiter wells. The sandwich ELISA involves attaching antigen to the solid phase by capturing it with an antibody that is bound to the microtiter wells.

The binding of proteins and other molecules to plastic results from hydrophobic interactions between non-polar protein regions and a nonpolar plastic surface. Although this binding is non-covalent, the loss of bound materials usually does not affect an analysis as long as the proper control are run. The actual binding capacity of a microtiter well is 200 to 300 ng of protein. Since binding to plastic is non-specific, it is extremely important to block all unoccupied sites with protein (e.g. BSA) or detergents (e.g. Tween-20) for preventing non-specific adsorption of enzyme-antibody conjugations.

The principle of the following protocol is that Anti-PHB IgG is first coated on microtiter wells. PHB is then anchored to the wells through binding to Ab. The Anti-PHB IgG labeled with biotin is bound to PHB by Ag-Ab interaction. Then avidin is added, which binds biotin. Then add Alkaline phosphatase labeled with biotin, which bind avidin through its biotin group. A soluble substrate is finally added for color reaction.

MATERIALS

10×TBS: NaCl 292.4 g,

Tris Base 24.2 g,

Total Volume 1000 ml in water.
1. Coating buffer: 0.1M carbonate buffer, pH 9.6.
   Stock solution A: 0.2M $Na_2CO_3$
   Stock solution B: 0.2M $NaHCO_3$
   80 mL solution A+170 mL solution B+250 mL water. Adjust pH to 9.6.
2. Washing buffer (TTBS): 0.5% Tween in 1× TBS.
3. Antibody Buffer: 0.25% BSA in TTBS.
4. Block solution: 1% BSA in 1× TBS.
5. Stock Antigen PHB suspension: prepared in water. To increase its stability, phospholipids are added and sonitation is applied.
6. Antibody (rabbit anti-PHB serum) purified through ImmunoPure IgG purification Kit (Pierce, Cat. No. 44667).
7. Sulfo-NHS-Biotin (from Pierce Cat. No. 21217).
   Stock solution: 100 mM, dissolve 50 mg in 1.1 mL dimethyl sulfoxide solution.
   Running solution: 20 mM in 100 mM biocarbonate buffer, pH, 8.0.
8. Alkaline phosphatase labeled with biotin:
   Alkaline Phosphatase: from Boehringer Mannheim Cat. No. 567744. 3 mg/0.3 mL, >2500 U/mg
   conjugation procedure: 60 uL running sulfo-NHS-biotin solution mixed with 100 uL enzyme preparation, incubate at room temperature for 4 hours.
9. Rabbit anti-PHB IgG labeled with biotin:
   3 mL (1 mg/mL) purified IgG was dialyzed against 100 mM biocarbonate buffer, pH. 8.0, was mixed with 200 uL 10 mM sulfo-NHS-Biotin running solution. Incubate at room temperature for 4 hours. Then dialyzed exhaustively against PBS (10 mM phosphate buffer, 0.15M NaCl, 0.02% $NaN_3$, pH 7.4).
10. Stock Avidin (from Sigma, Cat, No. A-9390 from egg white) solution: 5 mg avidin+0.2 ml 10× PBS+0.05 mL 2% $NaN_3$+0.75 mL $H_2O$+1 mL glycerol. Store at –5° C.
11. Alkaline phosphatase substrate kit: (from Bio-Rad, Cat. No. 172–1063). Soluble, for use in EIA systems that employ Ap-labeled Ab. The kit contains 100 5 mg tablets of p-nitrophenyl phosphorate and 100 mL of 5× diethanolamine buffer, which will prepare 500 mL of substrate solution. The above procedure gave less than satisfactory results. There is a need to pretreat the sample to release the PHB from lipids and proteins which may be physically interfering with the antibody reaction.

EXAMPLE 5

Immunoassay for PHB in Plasma Using $F(ab)_2$ fraction

PHB was determined by enzyme immunoassay on nitrocellulose membranes (0.2 μm) using the Bio-Rad Bio-Dot slot format apparatus. This system focuses the samples in a thin line which improves the quantification of the immunoassay results by densitometry. The method is essentially an ELISA assay using nitrocellulose as the solid phase. This medium has been found to give the most reliable results because the lipids and/or proteins in the LDL particles appear to inhibit the quantitative reaction of the PHB with its antibody in a traditional sandwich ELISA in which the antibody is found to wells. The PHB is retained by the nitrocellulose, and when the sheet is dried the PHB binds tightly. Washing apparently removes the protective substances and the reaction of the PHB antigen with the antibody is strong and reproducible.

PHB standards were prepared by sonicating a mixture of the polymer and phospholipids in buffer, and then adding this to plasma containing 0.02% sodium azide. This mixture was sonicated gently in a bath and then centrifuged. The supernatant is stored in small aliquots at –70° C. Reference samples are prepared from plasma which contains PHB in high, moderate and low concentrations. This is preserved with 0.02% sodium and stored as above.

PHB standards, references, and plasma samples are diluted with phosphate-buffered saline (PBS) and applied to wells in 200 μl buffer containing 2 μl to 0.125 μl plasma/well. This gave an immunoassay reading within the linear range for PHB (10 to 200 pg) in subjects with plasma PHB of 0.5 μg to 150 μg/dl. The range in normal adults in the pilot study was 1.8 to 48 μg/dl). Wells were blocked with gelatin in PBS, and the sheets are incubated with rabbit anti-PHB $F(ab')_2$. After washing with PBS Tween, sheets were incubated with alkaline phosphatase-IgG conjugate (goat anti-rabbit). Sheets were washed and treated with enzyme substrates BCIP (5-bromo-4-chloro-3-indolyl phosphate) and NBT (nitro blue tetrazolium) were added. On completion of the reaction, the sheets were washed with distilled water, dried and the results quantified with a densitometer. This procedure gave satisfactory results.

EXAMPLE 6

The range of concentrations of PHB in serum and the relationship between serum PHB and other serum lipids were examined using the procedure of Example 5. PHB concentrations were measured in serum samples of 55 young adults (29 men, 26 women; 22–43 years; mean age 27) for which lipid profiles were available. The values of PHB ranged from 1.8 to 24.2 µg/dl with a mean of 6.75 µg/dl. The mean value of PHB in the male sample was more than twice that for females (9.1 vs 4.2 µg/dl). Serum PHB in the male sample showed significant correlations with all other lipid fractions, with the exception of total glycerides (TG), and the strength of the association decreased in the order LDLC/HDLC>LDLC>TC/HDLC>-HDLC. Serum PHB in the female sample showed no significant relationships with other serum lipids.

The twenty-five fold variation in PHB in this relatively homogeneous group suggests that the range in the general population may be much larger. While the amounts of PHB are small compared to those of other lipids, concentration is not an important determinant in the genesis of a slow progressive disease such as atherosclerosis. There are many examples in medicine of minute concentrations of substances having strong and immediate physiological effects, e.g. hormones or toxins. More to the point, the long range effect of low concentrations of mutagens and other carcinogens on animals has become increasingly apparent, and legislation limiting human exposure to such compounds commonly focuses on the parts per billion range. It is possible then that the long term effect of even a small excess of this PHB in plasma could be its deposition in the endothelium and intima where it could serve as a nucleus for the accumulation of lipoproteins and cellular materials.

In summary, PHB is a ubiquitous component of the plasma lipoproteins, where it is concentrated in the atherogenic LDL fraction. PHB is an atherosclerotic agent and/or is an indicator of atherosclerotic risk.

EXAMPLE 7

Variation of the Immunoassay for PHB

Immobilon-AV Affinity Membrane™ (Millipore, Bedford, Mass.) is a polymeric membrane substrate which is chemically reactive with antibodies and other proteins, and binds them covalently with minimal loss of biological activity. The membrane was treated in coupling buffer (potassium phosphate) to covalently bind PHB-antibody, and remaining active groups were quenched with monoethanolamine (1% v/v) as directed. The membrane was washed with TBS and then placed on a Bio Dot monofiltration apparatus. Samples (serum, plasma or other) were diluted with TTBS (100 µl sample to 400 µl TTBS) and serial dilutions were prepared in TTBS. The samples (200 µl) were filtered by gravity flow through the antibody-coated membrane which recognizes and captures the PHB. One row of wells was reserved for blanks and PHB standards (10–100 pg). The wells were washed with TTBS (4×), and the membrane was then removed from the apparatus under vacuum, and incubated with the second antibody which was sheep anti-rabbit IgG conjugated to alkaline phosphatase, (F(ab')$_2$ fragment (Sigma), 1 µl/mL in 1% gelatin/TTBS for 30 minutes at room temperature. This antiserum had been preabsorbed with human serum proteins, human serum albumin and human IgG. After washes with TTBS (4×) and TBS (2×), color was developed with the enzyme substrate BCIP and NBT (Bio Rad alkaline phosphatase conjugate substrate kit). The reaction was stopped by adding distilled water. The amount of PHB was determined by comparison of the color generated with that of the standards.

EXAMPLE 8

Crotonic Acid Assay and NMR Assay for PHB

The PHB content of human serum lipoproteins obtained from a commercial source (Sigma). VLDL, LDL and HDL were assayed for PHB by the procedure of Law and Slepecky (Bluhm, T. L., et al., Macromolecules 19:2871 (1986)). As prescribed by this protocol, the lipoprotein samples (duplicates of two samples for each lipoprotein class) were digested with 6% sodium hypochlorite, a process which degrades most cellular substances but does not significantly affect PHB. The undigested residues were then washed sequentially with water, alcohol and acetone to remove excess reagent, water and most serum lipids. The remaining material was hydrolyzed in hot concentrated sulfuric acid (boiling water bath) to convert PHB to crotonic acid. The crotonic acid was quantitated by comparing the intensity of its absorption peak at 235 nm with that of standards. The identity of the crotonic acid was confirmed by GC-MS analysis using a Hewlett Packard 5995 Mass Spectrometer fitted with a 30.5 cm, 4.5 mm (i.d.) SP 1220/3% $H_3PO_4$ column. The results are summarized in the table below

| Fraction | SAMPLE 1 µg/mg prot | SAMPLE 2 µg/mg prot | AVERAGE µg/mg prot |
|---|---|---|---|
| VLDL | trace | trace | trace |
| LDL | 3.3 ± 0.5 | 5.1 ± 0.8 | 4.2 |
| HDL | 0.1 ± 0.05 | 0.3 ± 0.1 | 0.2 |

Finally, the identity of PHB in serum LDL was further confirmed by comparing the $^1$H NMR spectrum in chloroform solution with that of known PHB, using a Bruker WM 250 mHz spectrometer.

The concentration of PHB in the atherogenic LDL fraction prompted a search for the polymer in arterial plaque. Consequently, six samples of plaques which had been surgically removed from the carotid arteries of patients at Ingham Medical Hospital were assayed. Samples were digested, washed, and assayed by a variation of the procedure of Karr et al (Karr, D. G., et al., Appl. Environ. Microbiol. 46:1339 (1983)). This method is an order of magnitude more sensitive than the Law and Slepecky assay because the crotonic acid is purified by HPLC chromatography before it is quantitated, thus eliminating errors caused by background absorbance of contaminants. Furthermore, the hydrolysis in concentrated sulfuric acid is conducted at a lower temperature, and this lends to fewer breakdown products. Unfortunately, it also results in incomplete hydrolysis (85%) which requires a correction factor. In a modification of this protocol, samples were dried at 80° C. and then hydrolyzed with concentrated sulfuric acid at 90° C. for 30 minutes. The hydrolysate was diluted with a two and a half fold volume of concentrated sodium sulfate solution to reduce the viscosity of the acid solution and to convert the positively charged conjugate acid of crotonic acid to the neutral molecule. Crotonic acid was then extracted into methylene chloride, and sodium hydroxide (100 μl of 1N solution) was added to convert the volatile free acid to the non-volatile crotonate salt. The methylene chloride was evaporated with a stream of nitrogen gas, and the sample was then reacidified with dilute sulfuric acid and chromatographed on an HPLC organic acid column (Bio-Rad) using dilute sulfuric acid as eluent. The crotonic acid was quantitated by a comparison of peak area with those of standard samples of PHB treated by the same procedure. All six samples examined contained PHB in amounts which varied from 82 to 146 μg/g dry wt. or 61 to 118 μg/g wet wt. Though PHB constituted only a small part of these lesions, it was present in significantly larger amounts than in animal tissues (Reusch, R. N., Soc. Exp. Biol. Med. 191:377 (1989)).

EXAMPLE 9

Correlation Between PHB and Serum Lipids

The results of Example 7 led to a pilot study to examine correlations between serum PHB and serum lipids which are known risk factors for CVD, i.e. total cholesterol (TC), total triglycerides (TG), low density lipoprotein cholesterol (LDLC) and high density lipoprotein cholesterol (HDLC). The study was done in collaboration at the College of Human Medicine at Michigan State University using serum samples (fasting) which had been obtained from first year medical students as part of an entrance physical examination. Lipid profiles had been determined for these samples using a Kodak Ektachem DT 60 Eastman Kodak, Rochester, N.Y., with solid state slides. Controls were reference samples supplied by the manufacturer and samples exchanged with clinical laboratories from local hospitals. The remaining serum had been stored for less than a year in a −80° C. freezer. The samples were assayed for PHB by the modified assay of Karr et al (Karr, D. B., et al., Appl. Environ. Microbiol. 46:1339 (1983)) described above. There was only sufficient serum (ca 1 ml.) for one determination for each sample. A total of 56 samples were examined—30 men and 26 women. The range of PHB found in these samples was 1.8 to 47.8 μg PHB/dl serum. One sample with 47.8 μg PHB was identified by statistical analysis as an outlier and eliminated from the data before making the calculations listed below. In the tables below lipid values are given in mg/dl with the exception of PHB which is in μg/dl.

TABLE 1

NUMERICAL SUMMARIES OF ALL SUBJECTS:
Sample size = 55

| VAR | MEAN | MEDIAN | STDEV | MIN | MAX |
|---|---|---|---|---|---|
| Age | 26.6 | 27.0 | 6.81 | 22.0 | 43.8 |
| TC | 192 | 194 | 33.8 | 104 | 279 |
| TG | 121 | 104 | 76.3 | 33.0 | 416 |
| HDLC | 57.8 | 55.0 | 17.8 | 30.0 | 104 |
| LDLC | 112 | 109 | 33.3 | 46.0 | 193 |
| TC/HDLC | 3.69 | 3.50 | 1.41 | 1.70 | 8.20 |
| LDLC/HDLC | 2.21 | 2.20 | 1.10 | 0.54 | 6.40 |
| PHB | 6.75 | 5.50 | 4.72 | 1.80 | 24.2 |

Lipid profiles for males and females differ significantly (Reardon, M. F., Circulation 71:881–8 (1985)), and therefore the sample was divided into male and female groups. The descriptive statistics for the individual groups are given below.

TABLE 2

NUMERICAL SUMMARIES OF MALE SUBJECTS:
Sample size - 29

| VAR | MEAN | MEDIAN | STDEV | MIN | MAX |
|---|---|---|---|---|---|
| Age | 25.2 | 25.0 | 8.38 | 22.0 | 43.8 |
| TC | 202 | 208 | 28.9 | 163 | 279 |
| TG | 134 | 109 | 77.0 | 43.0 | 416 |
| HDLC | 51.3 | 50.0 | 6.9 | 30.0 | 104 |
| LDLC | 125 | 116 | 27.4 | 87.0 | 193 |
| TC/HDLC | 4.42 | 4.50 | 1.46 | 2.20 | 8.20 |
| LDLC/HDLC | 2.69 | 2.50 | 1.12 | 1.00 | 6.40 |
| PHB | 9.06 | 7.87 | 5.36 | 2.10 | 24.2 |

TABLE 3

NUMERICAL SUMMARIES OF FEMALE SUBJECTS
Sample size - 26

| VAR | MEAN | MEDIAN | STDEV | MIN | MAX |
|---|---|---|---|---|---|
| Age | 28.2 | 27.8 | 4.08 | 22.0 | 36.6 |
| TC | 181 | 187 | 35.8 | 104 | 251 |
| TG | 107 | 82.5 | 74.2 | 33.0 | 320 |
| HDLC | 65.0 | 60.0 | 16.2 | 41.0 | 99.0 |
| LDLC | 96.7 | 100.5 | 33.3 | 46.0 | 184 |
| TC/HDLC | 2.87 | 2.85 | 0.78 | 1.71 | 4.50 |
| LDLC/HDLC | 1.67 | 1.60 | 0.79 | 0.53 | 3.48 |
| PHB | 4.17 | 4.35 | 1.71 | 1.80 | 8.04 |

There is clearly a sexual bias in PHB levels as well as in lipid levels in the two experimental groups as is evident in the tests for difference of means (Table 4) determined from the t-statistic and p-values computed from normal distribution, for two-sided tests.

TABLE 4

TESTS FOR DIFFERENCE OF MEANS $H_o$: 1–2

| Variable | Observed Means M | F | t-Statistic | p-value |
|---|---|---|---|---|
| TC | 202 | 181 | 2.53 | 0.0170 |
| TG | 134 | 107 | 1.23 | 0.180 |
| HDLC | 51.3 | 65.0 | −2.89 | 0.0035 |
| LDLC | 125 | 96.7 | 3.48 | 0.0012 |
| TC/HDLC | 4.42 | 2.87 | 4.22 | <0.0001 |
| LDLC/HDLC | 2.69 | 1.67 | 4.14 | 0.0002 |
| PHB | 9.06 | 4.1 | 4.34 | <0.0001 |

The degree to which the experimental samples reflect the general population can be assessed by comparing the mean lipid values to the mean reference values in studies conducted by the Lipid Research Clinics (Reardon, M. F., Circulation 71:881–8 (1985)).

TABLE 5

REFERENCE VALUES FOR SERUM LIPIDS IN RELATION TO AGE

| | TC | TG | HDLC | LDLC | TC/HDLC | LDLC/HDLC |
|---|---|---|---|---|---|---|
| MEN | | | | | | |
| 20–24 yrs | 167 | 100 | 45 | 103 | 2.29 | 3.71 |
| 25–29 | 182 | 116 | 45 | 117 | 2.60 | 4.04 |
| 30–34 | 192 | 128 | 46 | 126 | 2.74 | 4.17 |

TABLE 5-continued

REFERENCE VALUES FOR SERUM LIPIDS IN RELATION TO AGE

|  | TC | TG | HDLC | LDLC | TC/HDLC | LDLC/HDLC |
|---|---|---|---|---|---|---|
| 35–39 | 201 | 145 | 44 | 133 | 3.02 | 4.57 |
| 40–44 | 207 | 151 | 44 | 136 | 3.09 | 4.70 |
| Exp Group 22.0–43.8 mean = 25.2 | 202 | 134 | 51 | 125 | 2.45 | 3.96 |
| WOMEN |  |  |  |  |  |  |
| 20–24 yrs | 172 | 89 | 53 | 104 | 1.96 | 3.25 |
| 25–29 | 176 | 89 | 56 | 110 | 1.96 | 3.14 |
| 30–34 | 179 | 89 | 56 | 111 | 1.98 | 3.20 |
| 35–39 | 187 | 94 | 55 | 120 | 2.18 | 3.40 |
| Exp Group 22.2–36.6 mean 28.2 | 181 | 107 | 65 | 97 | 1.49 | 2.78 |

The male experimental group varies significantly from the Reference group, primarily in its high HDLC, which suggests that the experimental group is somewhat less at risk for CVD than the general population. There is a much larger deviance in the female experimental group, with the high HDLC its most striking factor. As HDLC is the strongest predictor in women (Bush, T. L., et al., E. Clin. Chem. 34:8B (1988)), risk for the experimental sample appears to be lower than in the population at large. Correlation coefficients (Pearson) were determined for PHB and each of the other serum lipid fractions for the total sample and its male and female groups. The strength-of-association and significance of the correlations were also determined.

TABLE 6

TESTS FOR CORRELATION $H_o$: p = 0

1. ALL SUBJECTS: Sample size = 55

| Variables | Correl. coeff. | $R_2$ | t-statistic | p-value |
|---|---|---|---|---|
| PHB, TC | 0.419 | 0.176 | 3.360 | <<0.001 |
| PHB, TG | 0.238 | 0.057 | 1.784 | 0.0744 |
| PHB, HDLC | −0.421 | 0.177 | −3.379 | <<0.001 |
| PHB, LDLC | 0.516 | 0.266 | 4.385 | <<0.001 |
| PHB, TC/HDLC | 0.644 | 0.415 | 6.128 | <<0.001 |
| PHB, LDLC/HDLC | 0.672 | 0.452 | 6.606 | <<0.001 |

II. MALE SUBJECTS: Sample size = 29

| Variables | Correl. coeff. | $R_2$ | t-statistic | p-value |
|---|---|---|---|---|
| PHB, TC | 0.461 | 0.213 | 2.700 | ~0.01 |
| PHB, TG | 0.228 | 0.052 | 1.217 | 0.2 <p> 0.3 |
| PHB, HDLC | −0.433 | 0.187 | −2.817 | 0.1 <p> 0.02 |
| PHB, LDLC | 0.602 | 0.362 | 3.916 | <<0.001 |
| PHB, TC/HDLC | 0.583 | 0.340 | 3.729 | <0.001 |
| PHB, LDLC/HDLC | 0.737 | 0.543 | 5.665 | <<0.001 |

III. FEMALE SUBJECTS: sample size = 26

| Variables | Correl. coeff. | $R_2$ | t-statistic | p-value |
|---|---|---|---|---|
| PHB, TC | 0.105 | 0.0110 | <1 | NS |
| PHB, TG | 0.038 | 0.0014 | <1 | NS |
| PHB, HDLC | 0.150 | 0.0225 | <1 | NS |
| PHB, LDLC | 0.001 | 0.0000 | <1 | NS |
| PHB, TC/HDLC | 0.024 | 0.0005 | <1 | NS |
| PHB, LDLC/HDLC | −0.131 | 0.0172 | <1 | NS |

PHB levels in males in this sample correlate positively with TC, LDLC, TC/HDLC and LDLC/HDLC and negatively with HDLC. The strongest correlation is with LDLC/HDLC which is one of the strongest predictors of CVD risk in men (Kannel, W. B., Am. Cardiol. 52:9B (1983)). On the other hand, PHB levels in the female group show no correlation with serum lipids. In this age group, neither group is at high risk for CVD; however, the risk is less for women (Blackburn, H., In "Hypercholesterolemia and Atherosclerosis" (ed. Steinberg, D., et al) Churchill Livingstone, New York (1987)). The most reliable results were achieved using the ELISA procedure with nitrocellulose as the solid phase of Example 6. This assay is sensitive to 10 pg PHB and can quantitate the polymer in a few microliters of serum or plasma, has made a larger, more definitive investigation of the correlation between PHB and atherogenesis practical.

It was found that serum albumin tightly bound the PHB not contained in the LDL fraction. Thus, in Examples 3 and 7, the titer of the antibody was reduced by the step involving absorption with human serum albumin in determining the total PHB. However, the serum albumen treated antibody was used to accurately determine the PHB in the LDL.

In the improved procedure, the plasma was extracted with chloroform to remove the PHB in the LDL, and then the extracted PHB was determined with the antibody. This procedure determined the amount of PHB in the LDL. The antibody also was used to determine the total PHB in the serum. Total PHB can also be determined by chemical analysis. A ratio of LDL PHB to total PHB can then be determined and used as a predictor of the risk of arteriosclerosis This procedure was more precise than that of Examples 3 and 7.

Since lipids are generally transported in the plasma by lipoproteins, the distribution of PHB among plasma fractions was investigated to identify the carriers of this water-insoluble polymer. It was found that 20–30% of PHB is carried in the very low density (VLDL), and low density (LDL) lipoproteins, with most of the remainder carried by albumin, which irreversibly binds and solubilizes the PHB polymer for transport.

EXAMPLE 10

The procedures of Examples 3 and 7 were repeated except that the antibody to PHB and the antisera to PHB was not preabsorbed with serum albumin.

Materials and Methods

Materials and buffers. Plasma used for the survey of chloroform-extractable PHB was taken from samples drawn from medical students at Michigan State University, East Lansing, Mich., and stored at −80° C. for about a year (courtesy of Dr. Dennis Murray). The remaining plasma was obtained fresh (within 24 hours of drawing) from the Michigan Red Cross Regional Center in Lansing, Mich., and was maintained at 4° C. On receipt, the following preservatives were added: 0.01% sodium azide, 0.005% Gentamycin, 0.01% Thimerosal, 1 mM ethylenetriamine tetraacetic acid 9EDTA), 0.015% phenylmethylsulfonyl fluoride (PMSF) and the treated samples were stored at 4° C. TBS was 20 mM Tris HCl, pH 7.5, 500 mM NaCl; TTBS was 0.5% Tween 20 (Bio-Rad) in TBS; PBS was 137 mM NaCl, 2.7 mM KCl, 4.3 mM $Na_2HPO_4$, 1.4 mM $KH_2PO_4$. Human serum albumin (HSA) was purified (Calbiochem); bovine serum albumin 9BSA) was Fraction V (Sigma, St. Louis, Mo.).

Fractionation of plasma. Plasma was fractionated by density gradient ultracentrifugation. The method used was essentially that of Kelly and Kruski (Kelly, J. L. and Kruski, A. W., Meth. in Enz. 128, 170–181 (1986)). Plasma samples were adjusted to a density of 1.24 or 1.31 g/mL with NaBr (see Figures), and 2 to 4 ml placed in the bottom of 12×89 mm ultracentrifuge tubes. Step gradients were constructed with solutions of density 1.21 g/mL, 1.063 g/mL, 1.019 g/mL and 1.006 g/mL. These were prepared by dissolving NaBr in Milli-Q (Millipore, Bedford, Mass.) water containing 11.46 g/L NaCl, 0.372 g EDTA g/L, 0.13 g/L $NaN_3$ and 0.08 g/L Thimerosal (Sigma, St. Louis, Mo.). The densities were adjusted with the aid of a Abbe 2WA-J Refractometer (Shanghai, China). The samples were centrifuged at 14° C. at 38,000 rpm in an SWTi41 rotor for 36 to 48 hours in a Beckman Model L3-50 Ultracentrifuge (Beckman, Palo Alto, Calif.). Gradients were immediately divided into 0.6 mL fractions using an Isco Model 640 Density Gradient Fractionator (Isco, Lincoln, Nebr.), while the absorbance was continuously monitored at 280 nm with an Isco Model UA-5 Absorbance Monitor (Isco, Lincoln, Nebr.). The 280 nm absorbance of each fraction was measured with a Gilford Response UV Spectrophotometer (Gilford, Oberlin Ohio), and the densities were estimated from the refractive indices from a control gradient.

Isolation of PHB. Method 1. PHB was isolated by the method of Law and Slepecky (Law, J. H. and Slepecky, R. A., J. Bacteriol. 82, 33–36 (1961)). The sample was treated with alkaline hypochlorite (Clorox) (4 vol/vol) for 1 hour at 30° C. The PHB was recovered by centrifugation and washed sequentially with water, ethanol, and acetone. Method 2. PHB was recovered by four extractions with hot chloroform. The chloroform solution was filtered and the solvent was evaporated with a stream of dry nitrogen gas.

Chemical assay of plasma fractions for PHB. Fractions from NaBr gradients were dialyzed (3× against TE buffer and 1× against distilled water), and then lyophilized. The samples were hydrolyzed with concentrated sulfuric acid (1–2 mL) at 90° C. for 45 min to convert PHB to crotonic acid. Adipic acid (10 $\mu$g) was added as an internal standard, and the hydrolysate was then diluted with a three-fold volume of saturated sodium sulfate. Solid sodium sulfate was added, and the mixture was extracted 4× with methylene chloride. Crotonic acid was converted to the non-volatile salt by the addition of NaOH (100 $\mu$L of 1N), and the solvent was evaporated with a stream of purified nitrogen gas. The residue was reacidified with sulfuric acid, and chromatographed on a 300×7.8 mm Aminex HPX-87H column (Bio-Rad, Richmond, Calif.) using 0.014N $H_2SO_4$ as eluant; absorbance was monitored at 215 nm with a Bio-Rad Model 1305 UV Monitor. Crotonic acid was quantitated by comparing peak area, measured with a Shimadzu Model C-R3A Chromatopac Integrator (Shimadzu, Columbia, Md.), with that of standards (0.2–2 $\mu$g) which had been subjected to the same protocol.

Determination of cholesterol and triglycerides. After a 12 hour fast and abstinence from strenuous physical activity, each subject had a 7 mL blood sample drawn from an antecubital vein. The samples were cooled immediately to 4° C. and the cells were removed by centrifugation within one hour. Serum triglycerides and cholesterol were determined enzymatically using a Technicon SMAC (Technicon Instruments, Tarrytown, N.Y.). In this method, triglycerides are hydrolyzed with lipase (EC 3.1.1.3), and the glycerol product is treated with ATP and glycerol kinase to form ADP. The ADP is then treated with phosphoenolpyruvate and pyruvate kinase to form pyruvate. Finally, pyruvate is analyzed using the well-known NADH-NAD reaction catalyzed by lactate dehydrogenase. Cholesterol esters are hydrolyzed with cholesterol esterase to free cholesterol, and total free cholesterol is then oxidized to produce hydrogen peroxide that in turn is used to form a quinoneimine dye. The concentration of the dye, measured colorimetrically, is directly proportional to the cholesterol concentration in the plasma sample. Cholesterol in the high density lipoprotein fraction (HDL-C) was determined after precipitation of low density and very low density lipoproteins using a DuPont Automatic Clinical Analyzer (DuPont Co., Wilmington, Del.). Cholesterol in low density lipoproteins (LDL-C) was determined indirectly using the formula derived by Friedewald, Levy and Fredrickson (Friedewald, W. T., et al., Clin. Chem. 18, 499–502 (1972)). Measurements were made at the Laboratory of Clinical Medicine (Lansing, Mich.), which is accredited by the College of American Pathologists, and participates in the National Reference System for Cholesterol of the U.S. Department of Health and Human Services.

Preparation of PHB antibody. PHB (Sigma, St. Louis, Mo.) was purified by treatment with proteinase K (200 $\mu$/mL) and by precipitation from chloroform solution with 4 volumes methanol. The PHB was covalently bound to Keyhole Limpet haemocyanin using 1-ethyl-3-(dimethylaminopropyl) carbodiimide hydrochloride (EDC) and N-hydroxysulfosuccinimide (Sulpho NHS) (Pierce). The conjugated polymer was homogenized with Freund's adjuvant (Gibco), and antisera was raised in New Zealand White rabbits. The IgG fraction of the plasma was precipitated by the addition of ammonium sulfate (35%), redissolved in phosphate buffered saline, pH 7.0, and dialyzed overnight against the same buffer. The IgG was purified by chromatography on a column of protein A covalently coupled to cross-linked beaded agarose (Pierce e), and it was then adsorbed with Keyhole Limpet haemocyanin (Sigma) bound to agarose (cyanogen bromide-activated 4% cross-linked agarose; Sigma) until there was no significant reaction to the carrier protein. The F(ab')$_2$ fraction was prepared by digesting purified IgG with immobilized pepsin (Pierce, Rockford, Ill.) for 4 hours at 37° C., and purified by protein A chromatography and dialysis (Pierce F(ab')$_2$ Preparation kit).

Immunoassay for PHB. A dot-blot ELISA immunoassay (Catty D, and Raykundalia, C., in Antibodies Volume II, a practical approach" (Catty, D. ed). pp 97–154, IRL Press/ Oxford Univ. Press, GB (1989)) was used to determine PHB in plasma fractions. Samples were serially diluted with TBS buffer, and 10 to 150 $\mu$l portions of each dilution were applied to prewetted supported nitrocellulose-1 membrane (BRL, Gaithersburg, Md.) in a Bio-Dot apparatus (Bio-Rad, Richardmond, Calif.). The samples were allowed to filter through the membrane by gravity flow. Next, the membrane was heated at 90° C. for 30 minutes, and then washed with TBS and TTBS buffers. The membrane was blocked by incubation with 3% gelatin (Bio-Rad immunoassay grade) /TTBS for one hour at 37° C. Portions of the membrane to be used as controls (first antibody only, second antibody only) were cut off and treated separately. The remainder of the membrane was incubated with a solution of rabbit anti-PHB F(ab')$_2$ (in 1% gelatin/TTBS for 30 minutes at 37° C. After washes with TTBS, the membrane was incubated under the same conditions with the second antibody, which was goat anti-rabbit IgG (F(ab')$_2$) conjugated to alkaline phosphatase (Sigma, St. Louis, Mo.) (preadsorbed with human serum proteins, human IgG and human albumin). After washes, color was developed with the enzyme substrate 5-bromo-4-chloro-3-indolyl phosphate (BCP) and nitro blue tetrazolium (NBT) (Bio-Rad, Richmond, Calif.). The amount of PHB was determined by comparison of the color generated with that of PHB standards (10 to 100 pg).

PHB binding studies. The affinity of albumin for PHB was examined by following the transfer of $^{14}$C-PHB from chloroform into a solution of human serum albumin (HSA) in 10 mM Hepes, pH 7.2. $^{14}$C-PHB was sonicated and fractionated by HPLC chromatography on a size-exclusion column (Altex μ-Spherogel; 8 mm×30 cm). $^{14}$C-PHB was prepared by culturing *Azotobacter vinelandii* in medium containing 0.05 μCi/mL D-[U-$^{14}$C]-glucose (Amersham, Arlington Heights, Ill.) to stationary phase, and isolating PHB as previously described (Reusch, R. N. and Sadoff, H. L., J. Bacteriol. 156, 778–788 (1983)). $^{14}$C-A fraction of <15,000 MW was dissolved in 2 mL chloroform (9 μg/mL; 4150 cpm/μg) in a 25 mL corex screw-capped tube, and washed 3× with distilled water to remove any soluble labelled material. The chloroform solution was then overlayed with 3 mL of albumin solution. The layers were gently mixed on a Thermolyne (Barnstead/Thermolyne, Dubuque, Iowa) Speci-mix tube rocker, and at the designated periods 50 μl of the aqueous layer were added to 5 mL scintillation fluid (Safety-solve, rpi) and counted in a Beckman Model LS 7000 Scintillation Counter (Beckman, Palo Alto, Calif.).

Polyacrylamide gel electrophoresis and Western blots. Proteins were separated on duplicate one-dimensional discontinuous polyacrylamide gels by the method of Laemmli (SDS PAGE) (Current Protocols in Molecular Biology (Ausubel, F. M., Brent, R., Kingstom, R. E., Moore, D. D., Seidman, J. G., Smith, J. A. and Struhl, K eds). pp. 10.2–10.8 John Wiley & Sons, New York (1989)), using the Bio-Rad Mini-Protean II Electrophoresis Cell (Bio-Rad, Richmond, Calif.). The separating gel was 10% acrylamide (30% acrylamide/0.8% bisacrylamide, 0.1% SDS) and the stacking gel was 4% acrylamide. One gel wa stained to visualize the proteins (Silver stain-II Daiichi, Emprotech, Hyde Park, Mass.), and the proteins in the duplicate gel were electrophoretically transferred to nitrocellulose membranes in the Mini Trans-Blot Electrophoretic Transfer Cell (Bio-Rad, Richmond, Calif.). The nitrocellulose membrane was then probed for reaction with anti-PHB F(ab')$_2$ or anti-human albumin (Calbiochem, San Diego, Calif. goat antiserum) as described above.

RESULTS

Isolation of PHB. Lipoproteins can be classified into fractions based on their flotational density as very low density (VLDL) (<1.006 g/mL), low density (LDL) (1.006–1.063 g/mL) and high density (HDL) (1.063–1.120) (Mill, G. L. and Lane, P. A., A guidebook to lipoprotein technique. pp 1–76. Elsevier, N.Y. (1984)). To determine the distribution of PHB among lipoprotein classes, human plasma (pool from ten blood donors) was separated by density gradient ultracentrifugation into 20 fractions ranging in density from 1.005 to 1.24 g/mL. PHB is insoluble in water and common lipid solvents such as alcohol, acetone and ether, but it is soluble in chloroform. Consequently, each fraction was extracted several times with hot chloroform. Following removal of solvent, the PHB was assayed by hydrolyzing it to form crotonic acid, which was isolated by HPLC chromatography and quantitated by its UV absorption as described in Methods. This procedure can detect reliably as little as 10 ng PHB.

The distribution of PHB obtained with this protocol is shown in FIG. 2. Only LDL fractions contained significant amounts of PHB. The PHB peak did not coincide with the protein peak for LDL; the majority of PHB was in the heavier LDL particles ca 1.04–1.07 g/mL. This method may not completely resolve LDL subclasses; nevertheless, the LDL form a distinct yellow band, and the fractions containing the most pHB were consistently those at the tail end of the band. The VLDL and HDL lipoprotein fractions, and the protein fraction at the bottom of the gradient did not yield significant PHB.

Since these determinations were made using a pooled plasma sample, they yielded only average values for PHB. The range of plasma PHB concentrations in normal individuals was surveyed in 55 young adults, 29 males and 26 females. PHB was isolated from 1 mL plasma aliquots from each subject by repeated extraction with hot chloroform, and then determined as above. Presumably, this PHB derived mainly from the LDL fraction. On the strength of this presumption, the concentration of LDL-PHB showed great variability, ranging from 1.8 to 24.2 μg/dL. Table 7 summarizes the findings of the relationship of PHB to other lipid values.

TABLE 7

Numerical Summaries of PHB Extracted From Plasma of Normal Adults.

| VAR | MEAN | MEDIUM | STDEV | MIN | MAX |
|---|---|---|---|---|---|
| All Subjects: sample size = 55 | | | | | |
| Age | 26.6 | 27.0 | 6.81 | 22.0 | 43.8 |
| TC | 192 | 194 | 33.8 | 104 | 279 |
| TG | 120 | 104 | 74.7 | 33.0 | 416 |
| HDL-C | 56.7 | 52.4 | 18.0 | 30.2 | 105 |
| LDL-C | 111 | 109 | 33.1 | 46.0 | 193 |
| PHB | 6.75 | 5.50 | 4.72 | 1.80 | 24.2 |
| Male Subjects: sample size = 29 | | | | | |
| Age | 25.2 | 25.0 | 8.38 | 22.0 | 43.8 |
| TC | 202 | 208 | 28.8 | 163 | 279 |
| TG | 132 | 106 | 77.4 | 43.0 | 416 |
| HDL-C | 51.7 | 50.2 | 17.2 | 30.2 | 105 |
| LDL-C | 124 | 114 | 27.4 | 87.0 | 193 |
| PHB | 9.03 | 7.87 | 5.37 | 2.10 | 24.2 |
| Female Subjects: sample size = 26 | | | | | |
| Age | 28.2 | 27.8 | 4.08 | 22.2 | 36.6 |
| TC | 181 | 187 | 35.8 | 104 | 251 |
| TG | 107 | 84.5 | 70.6 | 33.0 | 320 |
| HDL-C | 62.2 | 58.7 | 17.5 | 37.8 | 99.4 |
| LDL-C | 96.8 | 100.5 | 33.4 | 46.0 | 184 |
| PHB | 4.20 | 4.35 | 1.74 | 1.80 | 8.04 |

Total cholesterol (TC), total triglycerides (TG), LDL cholesterol (LDL-C), HDL cholesterol (HDL-C), given in mg/dL, were determined as described in Methods. PHB, given in μg/dL, was extracted from plasma with chloroform and determined as described in Methods.

Separate profiles are exhibited for the male subjects, female subjects and for the combined sample. Group differences in mean levels were assessed by t-tests using a significance level α=0.05. The male and female groups do not differ significantly with respect to age and total triglycerides (TG). However, they differ with respect to total cholesterol (TC) (p-value=0.016) high density lipoprotein cholesterol (HDL-C) (p-value=0.029). Very significant differences are noted in low density lipoprotein cholesterol (LDL-C) and PHB levels. PHB levels also exhibit significant differences in variance. Table 8 exhibits Pearson correlation coefficients for PHB with some other plasma lipids.

TABLE 8

Correlation Coefficients of PHB with TC, TG, HDL-C, LDL-C and p-values for tests of $H_o$: = 0

| VARIABLE | TC | TG | HDL-C | LDL-C | TC HDL-C | LDL-C HDL-C |
|---|---|---|---|---|---|---|
| All Subjects: sample size = 55 | | | | | | |
| p-value | .419 | .246 | −.374 | .520 | .663 | .675 |
|  | .002 | .070 | .005 | <<.001 | <<.001 | <<.001 |

TABLE 8-continued

Correlation Coefficients of PHB with TC, TG,
HDL-C, LDL-C and p-values for tests of $H_o$: = 0

| VARIABLE | TC | TG | HDL-C | LDL-C | TC HDL-C | LDL-C HDL-C |
|---|---|---|---|---|---|---|
| Male Subjects: sample size = 29 | | | | | | |
| p-value | .460 | .247 | −.438 | .619 | .694 | .736 |
| | .012 | .196 | .018 | <<.001 | <<.001 | <<.001 |
| Female Subjects: sample size = 26 | | | | | | |
| p-value | .109 | .057 | .148 | .015 | .030 | −.010 |
| | NS | NS | NS | NS | NS | NS |

NS = not significant at α = .05. All analyses were carried out using SAS software, Version 6.04.

It is noted that none of these correlations are significant in the female group, but that HDL-C correlates negatively, and TCX and LDLC correlate positively with PHB in the combined group and in the male group. The most significant correlations are with LDL-C.

Determination of PHB by immunoassay. The protocol for PHB determination employed in the above studies is very arduous, and requires a minimum of 1 mL plasma for each measurement. To improve sensitivity and simplify the procedure, an immunoassay was developed. Antibodies were raised in rabbits to a PHB conjugate, and the F(ab')$_2$ fraction of the anti-PHB IgG was used in a dot-blot ELISA immunoassay (see Methods). This assay was a thousand fold more sensitive (ca 10 pg PHB) than the chemical assay and made possible determination with $\mu$L volumes. When plasma gradient fractions were analyzed with the immunoassay, a surprisingly different distribution pattern emerged (FIG. 2). PHB was again found in LDL fractions and it was absent in HDL; however, there was significant PHB in VLDCL, and the strongest positive reactions were in the fractions of highest density (>1.22 g/mL) (FIG. 2).

The distribution of PHB among VLDL fractions was somewhat variable (FIGS. 2, 3), but this may be due to the inability of the method of fractionate particles less density than physiological salt solution (1.006 g/mL). Nevertheless, the VLDL fractions clearly contained PHB in amounts that were roughly comparable to those in LDL. PHB in the VLDL was unique in that it slowly diminished in quantity when the fractions were stored at 4° C.; about half was degraded over a period of two weeks. In contrast, PHB in the LDL and high density fractions appeared stable. To sum up the results from determinations made for five plasma samples (each a pool of 10 to 15 individuals): 20 to 30% of total plasma PHB was found in lipoprotein fractions, 6–14% in VLDL, 8–16% in LDL, and <3% in HDL. The remainder was in the density protein fraction. This distribution pattern attests to the successful resolution of plasma into the four classes, VLDL, LDL, HDL and density protein, since the results are inconsistent with significant contamination of HDL or LDL by neighboring fractions.

There was considerable skepticism about the reliability of the immunoassay results because albumin, which is the major protein in the high density fraction, is known for its tendency to bind to a variety of substances (Peters, T., Adv. Prot. Chem. 37, 161–245 (1984)), thus giving false positive reactions. To confirm the presence of PHB in albumin, we attempted to isolate the polymer from commercial bovine serum albumin (BSA) by two methods in general use: 1) the method of Law and Slepecky (Law, J. H., and Slepecky, R. A., J. Bacterio. 82, 33–36 (1961)) in which alkaline hypochlorite is used to digest protein and most other cellular substances leaving PHB relatively unaffected, and 2) repeated extraction with hot chloroform. The putative PHB fraction recovered by these methods was hydrolyzed and the resulting crotonic acid quantitated by HPLC chromatography as above. Only 1.2 $\mu$g and 4.2 $\mu$g PHB were recovered from 1 g bovine serum albumin (BSA) by the first and second methods, respectively. This amount was less than 1% of what was indicated to be present by the immunoassay. Next, BSA was hydrolyzed directly without first isolating the polymer. This method gave a value of 440 $\mu$g PHB/g BSA, which was consistent with the immunoassay estimate of 485 $\mu$g. The PHB content of HSA determined by this protocol was 180 $\mu$g/g. These studies confirmed the presence of significant quantities of PHB in albumin, and revealed the strong and specific interactions between them that impede recovery of the polymer by classic methods.

In light of this binding, the distribution of PHB in density fractions of pooled plasma was re-examined, assaying fractions for PHB content by measuring crotonic acid produced by direct hydrolysis of dialyzed, lyophilized samples. This protocol (FIG. 3) indicated essentially the same distribution as the immunoassay, confirming its reliability. The immunoassay consistently gives slightly higher values; this may indicate that hydrolysis of albumin-bound PHB is less complete than that of the pure polymer.

These results indicate that the association of PHB with plasma fractions can be differentiated on the basis of solubility in chloroform. Extractable PHB resides mainly in LDL, so that it was only LDL-PHB that was measured in the survey detailed in Table 7. To determine the range of total plasma pHB in normal individuals, we used the immunoassay to survey 24 blood donors. The age and sex of these subjects were unknown. As shown in FIG. 4, total plasma PHB proved as variable as LDL-PHB with values extending from 0.6 mg to 18.2 mg/L (means 3.5 mg/mL) (FIG. 5).

Protein-PHB binding. The proteins in the high density fractions were subjected to Western blot analysis to identify the PHB-binding entities. The proteins were separated by electrophoresis on denaturing acrylamide gels (SDS-PAGE), and were then electrophoretically transferred to nitrocellulose membranes, and probes with anti-PHB F(ab')$_2$ (FIG. 6). The broad band at 65–70K was identified as albumin by molecular weight, by comparison of electrophoretic mobility with known HSA and with BSA in the molecular weight standards, and by probing the membrane with anti-human albumin. A second protein at ca 50K gave a weaker but significant reaction. There are a number of plasma proteins in this molecular weight range with unknown functions (Schwick, H. G., and Haupt, H., in The Plasma Proteins, Vol IV pp 168–220. Academic Press, New York (1984)). One or more of these may be involved in PHB metabolism or transport.

Albumin-PHB binding. The affinity of albumin for PHB was examined in vitro. A chloroform solution of $^{14}$C-PHB was gently mixed with an aqueous solution of albumin, and the transfer of $^{14}$C-PHB into the aqueous layer was followed by measuring the appearance of radioactivity in the aqueous phase (FIG. 6). The solubilization of PHB by albumin was slow; there was a lag of about an hour, and it required approximately 30 hours to reach equilibrium. About 35% of total PHB was solubilized by 10 mg/ml HSA, and 62% by 40 mg/mL BSA. Since PHB is ordinarily insoluble in water and soluble in chloroform, its transfer into an aqueous phase underscores the high affinity of albumin for pHB. Almost all the $^{14}$C-PHB (95%) precipitated in cold 5% trichloroacetic acid which rules out the possibility that PHB was degraded to water soluble products by the albumin or contaminating esterases.

Subsequently, the recovery of $^{14}$C-PHB from the $^{14}$C-PHB-HSA complex was attempted using the two procedures described above, while following the fate of $^{14}$C-PHB at each step (Table 9).

TABLE 9

Recovery of $^{14}$C-PHB From Human Serum Albumin.

Method 1 - Digestion with alkaline hypochlorite[a]

| | % Total Lost in Each Step |
|---|---|
| NaHCLO$_3$ treatment | 87.6 |
| Alcohol wash | 11.8 |
| Acetone wash | 0.3 |
| $^{14}$C-PHB recovered - 0.3% | |

Method 2 - Extraction of PHB with hot chloroform

| | % Total Recovered in Each Step |
|---|---|
| CHCl$_3$ extract 1 | 0.8 |
| CHCl$_3$ extract 2 | 0.2 |
| CHCl$_3$ extract 3 | 0.1 |
| $^{14}$C-PHB recovered - 1.1% | |

[a]Sample was digested with 7 mL alkaline hypochlorite (Clorox) at 30° C. for 1 hour. The undigested residue was collected by centrifugation, and washed sequentially with 2 mL volumes of alcohol and acetone.
In the method of Law and Slepecky (Law, J. H. and Slepecky, R. A., J. Bacteriol. 82, 33–36 (1961)), digestion with alkaline hypochlorite failed to release PHB from albumin and the polymer remained solubilized in the aqueous supernatant. Apparently, albumin complexed to pHB was protected from hydrolysis. The small amount of $^{14}$C-PHB in the residue was nearly all lost in the subsequent washes. Extraction of $^{14}$C-PHB from the albumin complex with boiling chloroform was slightly more successful, but only a small percentage of the total PHB was recovered. These results agree well with the above findings, and confirm the affinity of albumin for PHB, even under strongly denaturing conditions.

DISCUSSION

Since PHB is a ubiquitous constituent of cell membranes, it is not surprising to find it in the plasma. However, the irregular distribution of PHB among plasma fractions suggests that the polymer is not just a solute in the lipid milieu, but rather it is transported by specific carrier molecules. It was found PHB in VLDL and LDL, but it was virtually absent in HDL. By far the majority of PHB was in the serum albumin, which complexes and solubilizes PHB for transport in the circulation.

PHB has escaped detection, despite extensive examination of lipids in plasma, because of its physical properties and composition, as well as its low concentrations. PHB is not only extremely insoluble in water, but it also does not dissolve in many of the organic solvents used to extract lipids, such as alcohol, acetone, hexane and ether. Consequently, the usual procedures for extracting lipids do not remove significant amounts of PHB. It was found that the methods developed for isolating PHB from bacterial cells are often unsuccessful in recovering PHB from plasma components. PHB forms strong complexes with various cellular substances by virtue of the ability of its ester carbonyl oxygens to form hydrogen-bonds, and to function as ligands in coordination complexes. Complexation alters its solubility in unpredictable ways, sometimes rendering it insoluble even in the chloroform, and in others making it water soluble. Adding to these difficulties is the absence of distinctive atoms or moieties to facilitate detection. PHB is customarily analyzed by converting it to its unique degradation product, crotonic acid, which is measured by its UV absorbance or by gas chromatography (Karr, D. B., Waters, J. K. and Emerich, D. W., Appl. Environ. Microbial. 46, 1339–1344 (1983)). It was found that PHB could best be detected and quantified in solutions using immunological methods; in solids samples, direct hydrolysis is recommended.

PHB may enter the circulation in chylomicrons and VLDL from ingested food and through endogenous synthesis (Hay, R., et al., in Biochemistry and Biology of Plasma Lipoproteins (Scanu A. M. and Spector, A. A. eds) pp. 1–51, Marcel Dekker, N.Y. (1986)). The amount of PHB in the VLDL and its distribution in VLDL subclasses may be a function of diet, postprandial phase, and genetic factors. Since PHB cannot be recovered from VLDL by extraction with chloroform, it appears that the polymer is complexed to proteins in these particles and not just 'dissolved' in the lipid core. As the particles are converted to LDL in the VLDL-IDL-LDL cascade (Eisenberg, S., Meth. in Enz. 129, 347–366 (1986)), PHB may be degraded and/or transferred (e.g. to albumin). The presence of esterases or depolymerases in VLDL, which may degrade PHB, is suggested by the lability of PHB in these fractions. Polymer that eludes these disposal mechanisms may remain in LDL. It appears that PHB accumulates in a sub-group of LDL, but more detailed studies are needed to confirm this because of the limited resolution afforded by single-tube density gradient ultracentrifugation. The association of PHB with LDL is exceptional in that the polymer can be separated from the particles by classic methods, and this characteristic affords a method of determining LDL-PHB in whole plasma. The relative ease with which the PHB can be recovered suggests it is 'dissolved' in the lipid milieu of LDL or complexed to hydrophobic proteins. The PHB recovered from the density fractions must be contained within lipoproteins because 'free' polymer, such as might be liberated by the high centrifugal force, sediments at much higher densities (Nickerson, K. W., App. Envir. Microbiol. 43, 1208–1209 (1982)). There are other possible origins of LDL-PHB; the particles may be part of LDL that is produced directly (Steiner, G., et al., Meth. in Enz. 129, 395–420 (1986)), or PHB may actually be contained in Lp(a), the atherogenic lipoprotein of unknown origin, that is also found in this density range (Fless, G. M., and Scanu, A. M., in Biochemistry and biology of Plasma Lipoproteins (Scanu, A. M. and Spector A. A. eds) pp. 73–83, Marcel Dekker, N.Y. (1986)). The strong positive correlations found in males between LDL-PHB and LDL cholesterol, and the negative correlation with HDL cholesterol, suggest that PHB may be atherogenic.

The major carrier of PHB in plasma is albumin, which solubilizes the polymer and binds it irreversibly. The complete amino acid sequence and the tertiary structure of albumin is known (Mills, G. L. and Lane P. A., A guidebook to lipoprotein technique. pp 1–76. Elsevier, N.Y. (1984)), as is its crystal structure (Carter, D. C. and He, X. M., Science 249, 302–303 (1990)). The molecule has three heart-shaped domains that serve to bind small organic molecules that have a low water solubility, and thereby facilitate their movement through the circulation. Since PHB is uncharged, we assume it is bound to hydrogen bond donors such as serine, threonine and tyrosine, and by virtue of hydrophobic interactions in the interior of the globular protein. It was found that the rate of binding was slow, exhibiting a lag period of about an hour, which suggests that rearrangement or denaturation preceded binding. In vivo, the process may be facilitated and accelerated by transfer proteins.

It is intended that the foregoing description be only illustrative of the present invention and that the present invention be limited only by the hereinafter appended claims.

I claim:

1. A method for preparing an antibody against poly-beta-hydroxybutyrate, referred to as PHB, which comprises:

(a) providing deproteinated PHB;

(b) disrupting the PHB in water to form an aqueous suspension of segments of the PHB;

(c) centrifuging the suspension to remove solids and provide a supernatant containing suspended segments of PHB;

(d) coupling the suspended segments to an invertebrate hemocyanin to provide a conjugate;

(e) injecting a mammal with the conjugate in suspension; and (f) isolating an antibody against poly-beta-hydroxybutyrate from the blood of the mammal.

2. The method of claim 1 wherein the animal is a rabbit.

3. The method of claim 1 wherein the invertebrate hemocyanin is keyhole limpet hemocyanin and the PHB is from *Azotobacter vinelandii*.

4. The antibody produced by the method of claim 1.

5. The method of claim 1 wherein in addition the antibody is treated with an enzyme to remove portions of the antibody which are unnecessary for binding with the PHB.

6. The method of claim 5 wherein the enzyme is pepsin to produce a $F(ab')_2$ fraction which binds to the PHB.

7. The method of claim 5 wherein the enzyme is papain to produce a F(ab) fraction which binds to the PHB.

8. The antibody produced by the method of claim 5.

9. The antibody produced by the method of claim 6.

* * * * *